US012622662B2

(12) United States Patent
Oakes et al.

(10) Patent No.: US 12,622,662 B2
(45) Date of Patent: May 12, 2026

(54) PROTECTIVE SHIELD FOR RADIOLOGY SCANNERS

(71) Applicant: Wisconsin Alumni Research Foundation, Madison, WI (US)

(72) Inventors: Terrence R Oakes, Middleton, WI (US); Azam Syed Ahmed, Madison, WI (US); Joseph A Kiel, Newport, MN (US); Jordan Henry, Oregon, WI (US); Andrew Culp, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 39 days.

(21) Appl. No.: 17/378,860

(22) Filed: Jul. 19, 2021

(65) Prior Publication Data

US 2022/0022829 A1 Jan. 27, 2022

Related U.S. Application Data

(60) Provisional application No. 63/054,481, filed on Jul. 21, 2020.

(51) Int. Cl.
| | |
|---|---|
| *A61B 46/00* | (2016.01) |
| *A61B 6/00* | (2024.01) |
| *A61B 46/10* | (2016.01) |
| *A61B 50/00* | (2016.01) |

(52) U.S. Cl.
CPC ............ *A61B 6/4423* (2013.01); *A61B 46/10* (2016.02); *A61B 46/40* (2016.02); *A61B 2050/002* (2016.02)

(58) Field of Classification Search
CPC .. B32B 1/02; B32B 1/08; B32B 27/00; B32B 2307/412; Y10T 428/1352; Y10T 428/139; Y10T 428/31504; A61B 2050/002
USPC ...................................... 428/34.1, 36.9, 411.1
See application file for complete search history.

(56) References Cited

U.S. PATENT DOCUMENTS

| | | | | |
|---|---|---|---|---|
| 5,493,844 | A | * | 2/1996 | Combrink ............ B65D 31/142 |
| | | | | 53/410 |
| 2008/0216844 | A1 | * | 9/2008 | Olfert .................... A61B 46/10 |
| | | | | 128/856 |
| 2013/0092177 | A1 | * | 4/2013 | Chua ...................... A61B 5/055 |
| | | | | 53/429 |
| 2014/0275973 | A1 | * | 9/2014 | Schuele ................. A61B 5/702 |
| | | | | 600/415 |
| 2016/0135896 | A1 | * | 5/2016 | Fink ....................... A61B 5/055 |
| | | | | 600/410 |
| 2018/0164391 | A1 | * | 6/2018 | Rapoport ............... A61G 11/00 |
| 2019/0328476 | A1 | * | 10/2019 | Thompson ........... A61B 6/4423 |
| 2020/0054299 | A1 | * | 2/2020 | Daley, II ............... A61B 6/547 |

FOREIGN PATENT DOCUMENTS

| | | | | |
|---|---|---|---|---|
| JP | H11107164 | A | * | 4/1999 |
| WO | WO-2007106730 | A1 | * | 9/2007 |
| WO | WO-2018071720 | A1 | * | 4/2018 |

* cited by examiner

*Primary Examiner* — Michael C. Romanowski
(74) *Attorney, Agent, or Firm* — Boyle Fredrickson, S.C.

(57) ABSTRACT

A shield for the bore of radiology scanners provides a resilient sheet material that can be compressed against the inner surface of the bore by a circumference expander greatly simplifying installation.

18 Claims, 6 Drawing Sheets

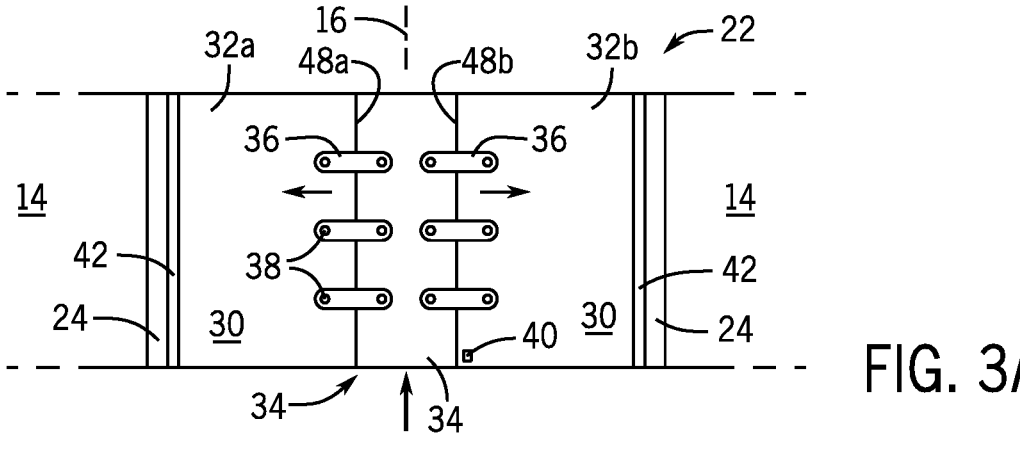
FIG. 3A
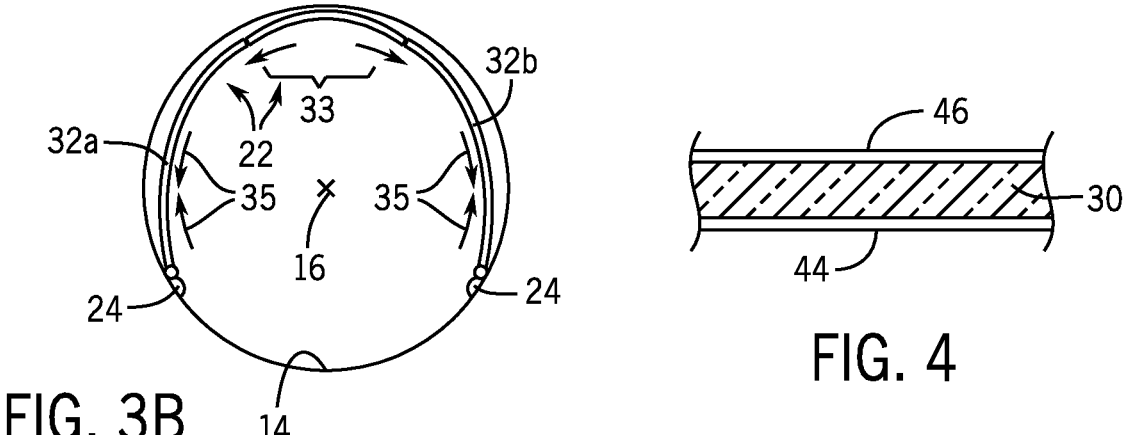
FIG. 3B
FIG. 4
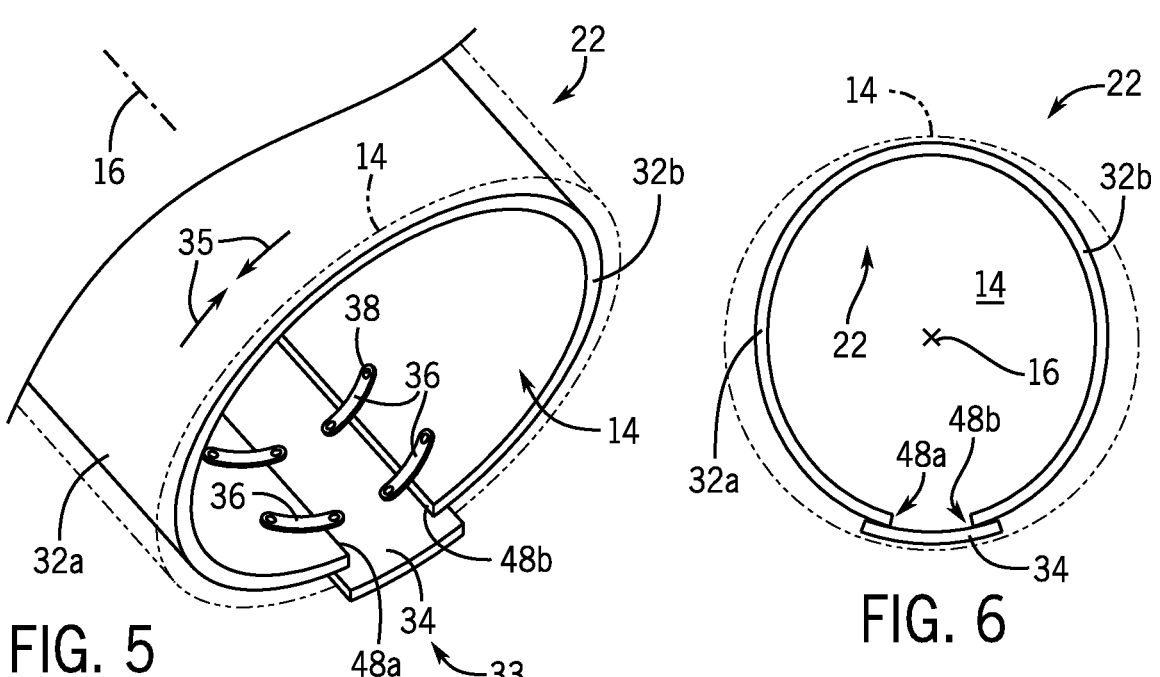
FIG. 5
FIG. 6

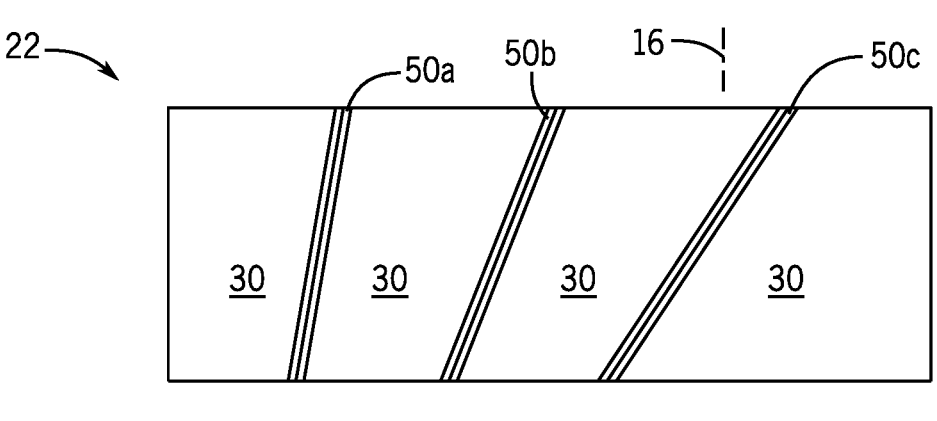
FIG. 10
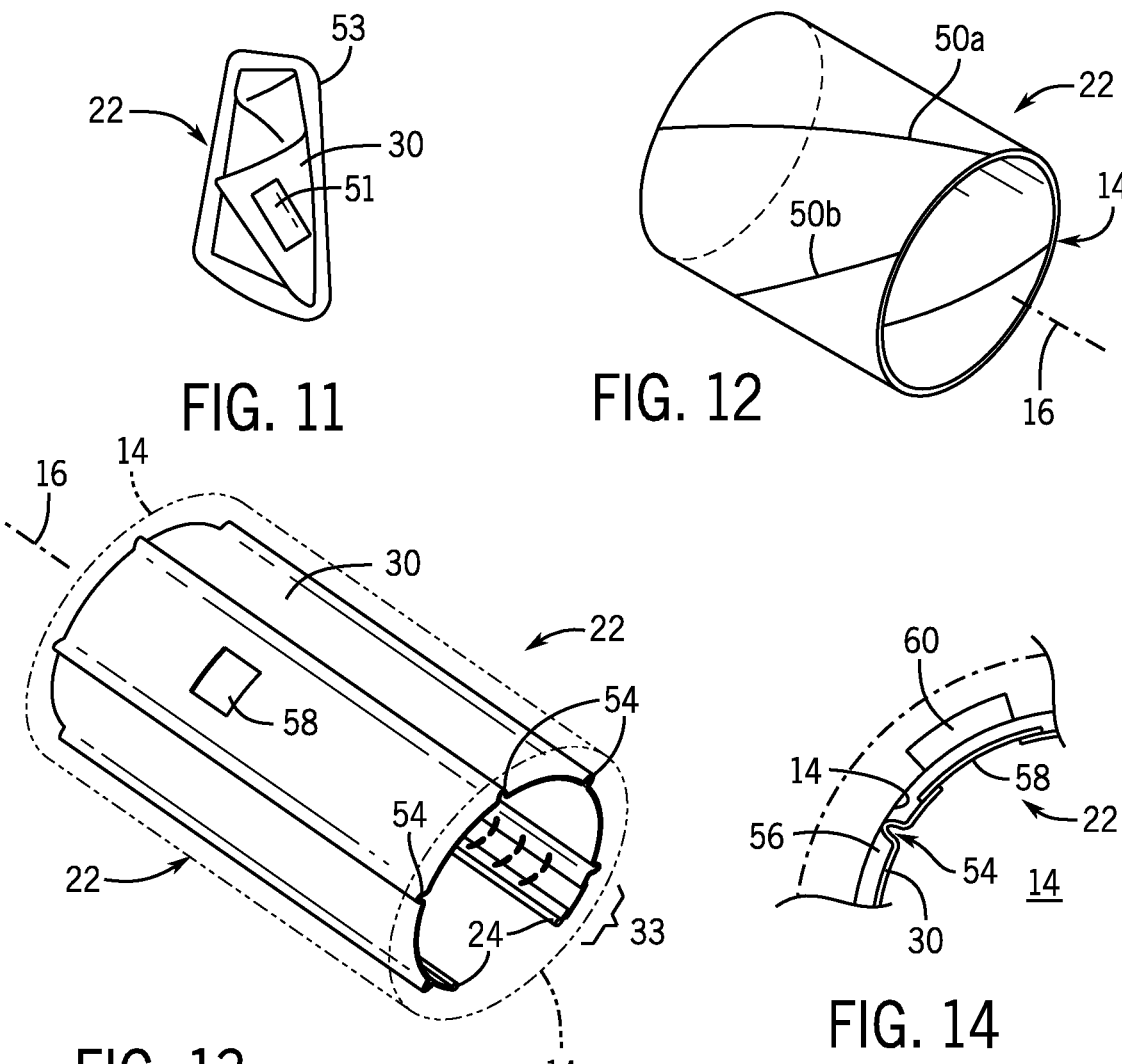
FIG. 11
FIG. 12
FIG. 13
FIG. 14

PROTECTIVE SHIELD FOR RADIOLOGY SCANNERS

CROSS REFERENCE TO RELATED APPLICATION

This application claims the benefit of U.S. provisional application 63/054,481 filed Jul. 21, 2020 and hereby incorporated by reference.

STATEMENT REGARDING FEDERALLY SPONSORED RESEARCH OR DEVELOPMENT

This invention was made with government support under CA177205 awarded by the National Institutes of Health. The government has certain rights in the invention.

BACKGROUND OF THE INVENTION

The present invention relates to protective medical shields and in particular to a medical shield for radiology scanners such as CT machines, MRI machines, PET machines, etc. where the patient is received within a bore.

Radiology scanners have proven to be important tools in identifying and managing the treatment of patients with novel infectious diseases, such as COVID-19. When radiology scanners are used with an infected patient, the scanner itself can become a fomite, or point-source for transmission of infectious agents to other patients using the scanner. For this reason, thorough cleaning of the scanner after such patience is required.

Unfortunately, cleaning of a scanner can be time-consuming, in some cases taking over one hour. This delay, preventing other use of the scanner during the cleaning process, increases medical costs and significantly reduces the availability of the radiology scanner, something that is particularly a problem in an Emergency Room (ER) setting, where immediate access to scanners can be critical.

In order to simplify the cleaning process, and/or to mitigate transmission of infectious agents to a patient, it is known to install fabric-like surgical drapes so as to cover the surfaces of the bore of the radiology scanner receiving the patient. Installing a standard surgical drape on the curved interior surface of the bore of a radiology scanner is difficult, may offer only irregular protection, and in some cases may be as time-consuming as cleaning the bore. Large patients, as they are moved in and out of the narrow scanner bore may distort or tear such drapes away from the bore. Loose or poorly secured drapery may also interfere with interventional procedures and with movement and observation of patients.

SUMMARY OF THE INVENTION

The present invention provides a specialized shield for radiology scanner bores employing a thin sheet of self-supporting, semi-rigid material. While thicker material of this type is not normally considered for disposable drapes, the ability to quickly and effectively place this material over the bore surfaces can make it more cost-effective than managing thinner fabric-like materials. Providing a specialized disposal bag with the shield accommodates the fact that the stiffer shield material is not as easily compacted for disposal.

In one embodiment, the invention provides a shield for a medical scanner having a sterile resilient sheet sized to fit loosely within the bore of a medical scanner in a first relaxed state and then to flex outward against an inner circumference of the bore in a second compressed state upon circumferentially directed compressive forces on the resilient sheet, the resilient sheet in the second state extending along an axial length of the bore and over at least 50% of a circumference bore.

It is thus a feature of at least one embodiment of the invention to provide a shield for protecting the bore of a radiology scanner having greatly simplified installation facilitated by a natural resiliency of a constituent plastic sheet of the shield.

The resilient sheet may be self-supporting on opposed edges against inner walls of a 20 inch diameter cylindrical bore.

It is thus a feature of at least one embodiment of the invention to allow localized compressive forces to expand the shield against the bore.

The shield may include an inner coating of hydrophilic polymer.

It is thus a feature of at least one embodiment of the invention to provide a coating that aids in trapping and retaining moisture from a patient's breath that may carry infections.

The resilient sheet may include an inner, antimicrobial coating.

It is thus a feature of at least one embodiment of the invention to actively reduce the transfer of bacteria and viruses from the patient via the bore and shield.

The shield may further include an outer coating of a releasable adhesive over some or all of the outer surface.

It is thus a feature of at least one embodiment of the invention to provide improved resistance to dislodgment of the shield without the normal problems of adhesives on a highly flexible material that can fold over on itself during installation.

The resilient sheet may have, in the first state, a first and second circumferentially spaced edge in the shield and may further include a connector adjustably joining first and second circumferentially spaced edges to change the separation between the first and second circumferentially spaced edges to provide the circumferential compression of the second state.

It is thus a feature of at least one embodiment of the invention to allow the shield to be pressed against the inner surface of the bore to reduce interference with the patient, maximize the opening of the bore, and provide improved bracing against dislodgement.

The connector may provide a single actuator member extending along the bore and movable along the bore between a first and second state to cause the first and second circumferentially spaced edges to move between a first separation with the resilient sheet fitting within the inner circumference of the bore without pressing against that circumference to a second separation with the resilient sheet pressed against the inner circumference of the bore.

It is thus a feature of at least one embodiment of the invention to provide a rapid and convenient mechanism for tightening the shield against the bore that can be implemented from one end of the bore, for example, with one simple motion.

The actuator member may be a panel extending parallel to the axis of the bore along an inner wall of the bore and flexible to conform to the cylindrical bore.

It is thus a feature of at least one embodiment of the invention to provide a connector system that can employ conforming, light weight, and disposable or recyclable materials.

The single actuator member may provide multiple points of contacts along the axial length of the panel to the first and second circumferentially spaced edges to provide circumferential expanding force along the at least one resilient sheet.

It is thus a feature of at least one embodiment of the invention to permit a simultaneous tightening of the shield to the bore along multiple axially separated locations.

The shield may further include a lock holding the single actuator member with respect to the first and second circumferentially spaced edges in the second state.

It is thus a feature of at least one embodiment of the invention to provide a connector system that can be locked in place without necessarily being bi-stable.

The lock may be selected from the group consisting of a hook and loop fastener and a pressure sensitive adhesive joining the actuator member and at least one of the first and second circumferentially spaced edges of the resilient sheet.

It is thus a feature of at least one embodiment of the invention to provide a simple and easily sterilized radiolucent lock mechanism compatible with a disposable shield.

The axial movement of the single actuator member may provide a change in separation of the first and second circumferentially spaced edges of at least one inch between the first and second state.

It is thus a feature of at least one embodiment of the invention to permit a substantial amount of adjustment to accommodate variations in bore size.

It is thus another feature to provide ample difference in circumference between the scanner bore and the disposable shield for facile and rapid installation and removal.

The single actuator member may communicate with the first and second circumferentially spaced edges through a set of toggle links.

It is thus a feature of at least one embodiment of the invention to provide a simple mechanism compatible with radiology scanners and offering a high degree of adjustability and progressively increasing mechanical leverage.

The resilient sterile plastic sheet material may include at least one panel of an air-permeable filter material.

It is thus a feature of at least one embodiment of the invention to provide a shield that is compatible with radiology machines providing for in-bore air circulation.

In one embodiment, the outer surface of the resilient sheet includes a plurality of ribs to provide an air gap between the resilient sheet and the bore in the second state.

It is thus a feature of at least one embodiment of the invention to accommodate radiology machines that require in-bore airflow for cooling or the like.

The resilient sterile plastic sheet may include hinges extending along an axis of the bore allowing for non-resilient folding of at least one resilient sterile plastic sheet.

It is thus a feature of at least one embodiment of the invention to permit a reduction of the size of the un-deployed shield for shipping or storage when a resilient material is used.

The hinges may follow helical lines with respect to the cylindrical bore in the second state.

It is thus a feature of at least one embodiment of the invention to provide for a self-locking of resilient hinges as they are formed into a helical arch against the inner surface of the bore.

The resilient sterile plastic sheet may be transparent.

It is thus a feature of at least one embodiment of the invention to allow ready inspection of the bore and reduce a sense of confinement that might occur with darker or opaque materials.

These particular objects and advantages may apply to only some embodiments falling within the claims and thus do not define the scope of the invention.

BRIEF DESCRIPTION OF THE DRAWINGS

FIGS. 3a and 3b are figures similar to FIGS. 2a and 2b showing the shield in an expanded state fitting tightly against the bore;

FIG. 4 is a fragmentary cross-section of the shield material showing optional outwardly facing adhesive and inwardly facing hydrophilic and/or antimicrobial layers;

FIG. 5 is a fragmentary perspective view of the bore in phantom and a second embodiment of the shield suitable for radiology scanners without guide rails;

FIG. 6 is an elevational cross-section of the shield of FIG. 5 in a bore in an expanded state;

FIG. 10 is a general depiction of shield material having multiple hinges that are tipped with respect to the longitudinal axis to provide resistance to folding along the hinge axis after installation;

FIG. 11 is a top plan view of the shield the FIG. 10 folded along the hinge lines and encased in a sterility-preserving package;

FIG. 12 is a simplified representation of the shield of FIG. 10 formed into a cylinder to conform to the bore of a radiology scanner showing the helical path of the hinge lines causing a curvature of the hinge lines providing stiffness against folding on the hinges after installation;

FIG. 13 is a perspective view of an alternative embodiment of the shield providing radially outwardly extending ribs spacing the shield to provide air passage between the shield and the bore of the radiology scanner and showing panels of air transmissive material;

FIG. 14 is a fragmentary elevational cross-section of the shield of FIG. 13 showing positioning of a panel of air transmissive material near a vent port in the bore;

DETAILED DESCRIPTION OF THE PREFERRED EMBODIMENT

Figure 1:
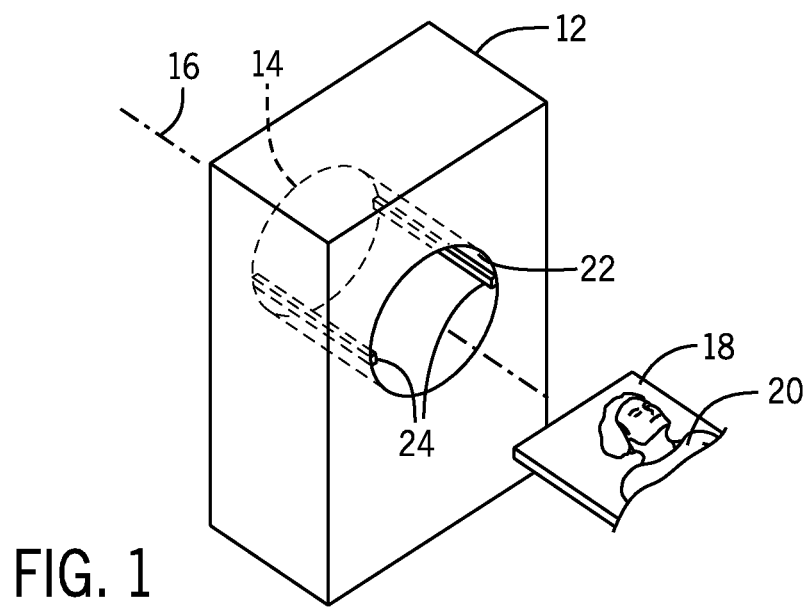
FIG. 1 is a simplified perspective view of a radiology scanner of a type having table guide rails within the bore showing a removable shield per the first embodiment of the invention.

Referring now to FIG. 1, a radiology scanner 10 such as a CT machine, PET machine, or MRI machine, may include a scanner housing 12 having a patient-receiving bore 14 having a cylindrical perimeter extending around a longitudinal axis 16. The bore 14 will be sized to receive a patient table 18 holding a patient 20 so that the patient 20 may be scanned within the bore 14. Generally, the diameter of the bore 14 is minimized, consistent with patient comfort, to provide closer range scanning and for this reason may have a diameter of as little as 16 inches. The longitudinal length of the bore may vary from approximately 30 inches to 60 inches Bores 14 for some types of radiology scanners 10, such as MRI machines, include longitudinally extending table guide rails 24 that receive and support edges of the patient table 18 when the patient table 18 is inserted into the bore 14. The guide rails 24 extend axially along the length of the bore and also radially inwardly in horizontal opposition from the inner walls and lower half of the bore 14. Such guide rails 24 are normally not found in CT or PET scanners which will be discussed below.

The present invention provides a removable shield 22 that may fit within the bore 14 to cover the inner walls of the bore 14 against contamination from infectious material. In a first embodiment, the removable shield 22 may extend from the upper edges of the table guide rails 24 and may cover the entire inner circumference of the bore 14 above and between the guide rails 24. In this respect, removable shield 22 will cover at least 50% of the inner surface of the bore 14 and surfaces above the patient table 18 to provide good protection against cross-contamination between patients 20 using the scanner 10.

Figure 2A:
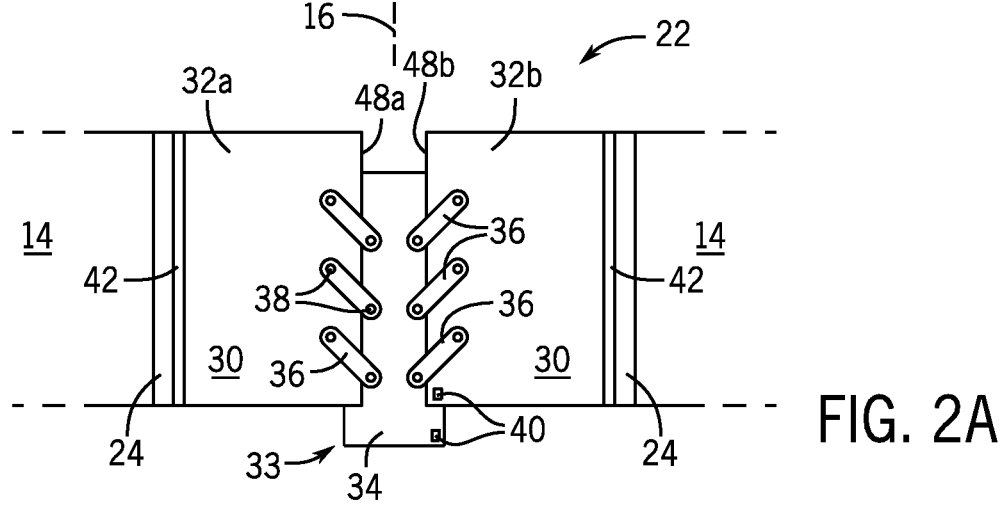
FIGS. 2a and 2b are fragmentary panoramic views about a longitudinal axis of the bore of the shield of FIG. 1 in a first relaxed state and an elevational cross-section of that shield in the relaxed state.
Figure 2B:
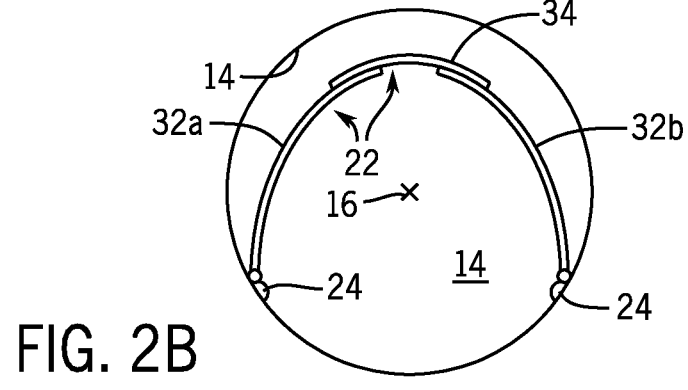

Referring now to FIGS. 2*a* and 2*b*, in an embodiment suitable for MRI machines having guide rails 24 as discussed above, the shield 22 may present a sterile, resilient sheet 30 divided into a first portion 32*a* and a second portion 32*b* each extending longitudinally by the longitudinal length of the bore 14 along axis 16. Each of the portions 32 may rest on and are supported by a respective guide rail and extend upwardly to or near an apex of the bore 14 to edges 48 where they are joined by a connector 33 that may adjust the separation of the upper edges 48 of the portions 32 by movement of an actuator member 34. Depending on the scanner machine characteristics and user preference, the connector may be placed anywhere circumferentially, including at the apex, or resting on the bed guide rail, or anywhere between those points.

The actuator member 34 may be a flexible panel formed of a similar or identical material to the portions 32 and may interconnect the portions 32 by means of a set of longitudinally spaced toggle links 36 extending from the actuator member 34 circumferentially to the left and the right of the actuator member 34. Each toggle link 36 is pivotally attached at one end to the actuator member 34 and at a second end pivotally attached, respectively, to different of the first and second portions 32, for example, by plastic rivets 38 or the like.

As depicted in FIGS. 2*a* and 2*b*, when the actuator member 34 is displaced longitudinally out of alignment with respect to the portions 32, the toggle links 36 are tipped to more closely align with the longitudinal axis 16 providing a relatively small gap circumferentially between upper circumferentially spaced edges 48 of portions 32*a* and 32*b*. In this state of the actuator member 34, the shield 22 formed of portions 32 and actuator member 34 may arc upwardly from the rails 24 in an elastic catenary spaced from the inner walls of the bore 14 (shown in exaggerated form in FIG. 2*b* and with the toggle links 36 removed for clarity).

Referring now to FIGS. 3*a* and 3*b*, in a second state, the actuator member 34 may be moved longitudinally rearwardly, as depicted, into longitudinal alignment with the portions 32 causing the toggle links 36 to extend more closely perpendicular to the longitudinal axis 16. This movement causes a separation of the circumferentially spaced upper edges 48 of the portions 32*a* and 32*b* and move the portions 32*a*, 32*b* and actuator member 34 apart so that the material of the shield 22 presses outwardly and is stabilized against the inner surface of the bore 14. This movement of the actuator member 34 causes a circumferential compression force 35 along the material of the portions 32 and actuator member 34 flexing the shield 22 outward against the bore 14 maximizing the space within the shield 22 and providing frictional bracing between the shield 22 and the bore 14. In this regard, the resilient sheet 30 and actuator member 34 are sufficiently stiff so as to not to buckle under the necessary compressive force 35 providing this conformal flexing and are essentially self-supporting on the rails 24 as braced by the bore 14.

It will be appreciated that this toggle mechanism of the toggle links 36 as so described provides a changing mechanical advantage with respect to separating the first and second edges 48, with initial movement of the actuator member 34 providing rapid separation of the edges 48 that quickly moves the shield 22 against the bore 14. Subsequent movement of the actuator member 34 provides a higher mechanical advantage as the toggle links 36 move to a more perpendicular orientation with respect to the longitudinal axis 16 which provides a higher degree of compression, thereby accommodating both rapid adjustment and high compression.

A lock mechanism 40 may be provided on the actuator member 34 and one of the portions 32 to hold the actuator member in the state shown in FIG. 3 without slippage. The lock mechanism, for example, may comprise two parts of a hook and loop listener (separately engaged on the actuator member 34 and one of the portions 32) which engage when the actuator member 34 is moved inwardly as shown in FIG. 3 or may be a pressure sensitive adhesive, or a snap, or other mechanical detent of types known in the art, positioned similarly. The longitudinal lowermost gasket strip 42, for example, an elastomeric gasket providing increased rigidity and frictional engagement with the rails 24, improves the stability to these lower edges that abut the rails 24.

Referring now to FIG. 4, the resilient sheet 30 forming portions 32*a* and 32*b* as well as actuator member 34 may be a thin transparent polymer material, for example, a high density polyethylene or acrylic material having a thickness sufficient to be self-supporting as described and typically of no less than 1/64 of an inch (or at least 0.4 mm) and in some cases at least 1/32 of an inch in thickness. As used herein, "self-supporting" refers to sheet that can be supported by opposite edges within a 16 inch diameter cylindrical bore over 50% of the circumference of that bore without buckling under the compressive force along the sheet. Desirably, the resilient sheet 30 may have a stiffness such that a material where an 8 inch long strip of the resilient sheet 30, 1 inch wide and suspended in horizontal cantilever from one end will deflect downward along its length under the force of gravity at the other end by less than 6 inches. The inventors contemplate that the resilient sheet 30 may also be constructed of paper or paper-like materials including composite materials such as paper or polymer materials combined with fibers such as fiberglass or the like.

An inner surface of the resilient sheet 30 may have a coating 44 that is hydrophilic, for example, having a material of the type used on catheters to create a slippery surface. In this case, however, the coating 44 operates to capture and immobilize water droplets from the breath of patient that could operate as vectors for transmission of infectious agents. In addition, or alternatively, the coating 44 may have antimicrobial properties to kill or capture bacteria, fungus and viruses which may incorporate materials such as antibiotics and viricides.

In some embodiments, the outer surface of the resilient sheet 30 may have a pressure sensitive releasable or repositionable adhesive 46, for example, localized in areas near the rails 24 to assist in installing the shield 22 and in providing resistance to accidental dislodgment once the shield 22 is expanded in the form shown in FIG. 3. Similar material may be used for the toggle links 36 which may have an increased thickness, for example, of greater than 1/16 of an inch.

Generally, the resilient sheet 30 will have a uniform thickness throughout the bore, however the invention contemplates that for some types of scanners for example CT and PET scanners which have an annular region in the center of the bore where the x-rays or gamma rays detectors are located, the sheet may be made thinner.

It will also be appreciated that in some embodiments the resilient sheet 30 and actuator member 34 may be opaque, and may furthermore have a color similar to the bore, or it may have a pattern or color printed upon such as decoration or scenery desirable for certain patient populations such as children.

Desirably the resilient sheet 30 and actuator member 34 will be free from conductive materials (that may promote eddy current flow), metals or magnetic materials, that may interfere with MRI systems and will be radiolucent to x-rays. In this latter regard these materials will have a total linear attenuation measured perpendicularly relative to the inner surface of the scanner bore when the materials are installed less than or equal to that of a thickness of 0.8 cm of distilled water.

Referring now to FIGS. 5 and 6, in a CT or PET radiology scanner 10, the bore 14 will typically not have rails 24. In this case, the first and second portions 32a and 32b may be parts of a continuous sheet of resilient sheet 30 with the connector 33 positioned to join first and second edges 48a and 48b of the continuous resilient sheet 30 and the toggle links 36 joining these edges 48 to the actuator member 34. Otherwise, the connector 33 operates in the manner shown in FIGS. 2 and 3 so that axially inward movement of the actuator member 34 into alignment with the portions 32 causes the edges 48a and 48b to separate, pressing the material of the portions 32 and actuator member 34 tightly against the inner surface of the bore 14. In this embodiment, the resilient sheet 30 and actuator member 34 will cover an entire circumference of the bore 14, and the compressive force 35 is formed from a pressing of the resilient sheet 30 and actuator member 34 broadly against the internal constraining bore 14 rather than in a concentrated pressure on the rails 24. In other respects this embodiment may be the same or employ various features described above. While the connector 33 is shown positioned at the bottom of the bore 14 for convenience, clearly the shield of FIG. 5 may be installed in any orientation within the bore 14 and may preferably be installed with the actuator member 34 at the apex of the bore inverted from that as shown.

Figures 7, 8, 9:
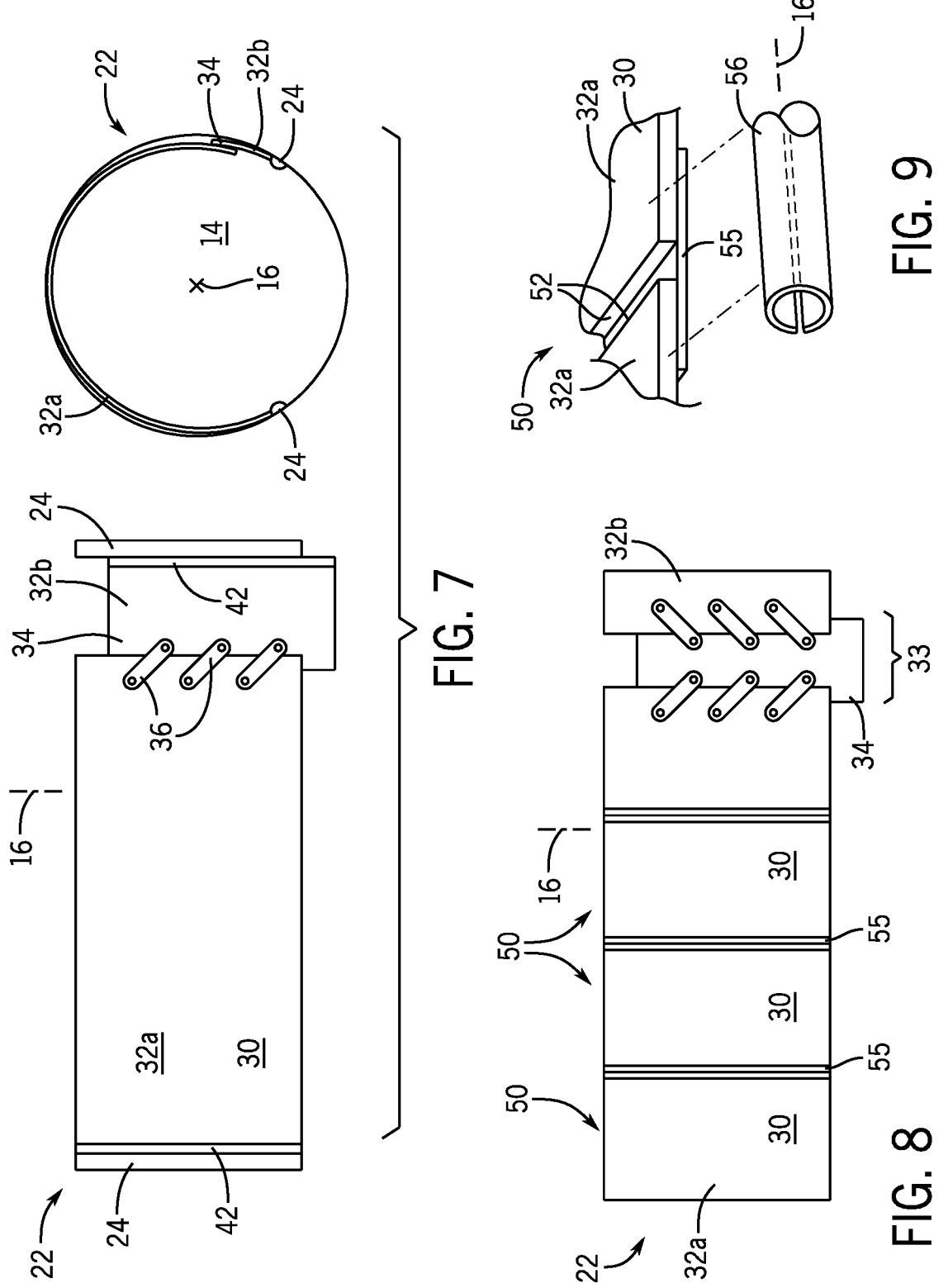
FIG. 7 shows an alternative embodiment of the shield in a relaxed state together with its elevational cross-section as installed in an expanded state using a simplified adjustment mechanism.
FIG. 8 is a figure similar to FIG. 7 showing an alternative embodiment of the inventions described above providing for a non-resilient hinge in the resilient sheet material.
FIG. 9 is a fragmentary, perspective exploded view of one hinge of FIG. 8 showing a stiffening rib that can be installed on the hinge at its longitudinally opposed edges.

Referring now to FIG. 7, it will be appreciated that a single set of toggle links 36 may be employed between the actuator member 34 and a first portion 32a of the resilient sheet 30 to provide the necessary compressive force 35 between rails 24, with the second portion 32b of the resilient sheet 30, resting on a rail 24, simply being an extension of material of the actuator member 34. The same observation holds for the continuous sheet without rails, i.e. for the CT or PET scanner embodiment. A disadvantage to this approach is that of shifting alignment of the first and second portions 32 as the actuator member 34 is adjusted.

Referring now to FIG. 8, the desired resiliency of the resilient sheet 30 may be provided, together with more compact shipping and storage of the shield 22, by dividing one or both of the portions 32 of the flexible plastic sheet with one or more non-resilient hinges 50. These hinges 50 may extend along a longitudinal hinge line and allow the resilient sheet 30 to be folded to a more compact configuration without the resistance to folding caused by the resiliency of the resilient sheet 30. Desirably, the hinges 50 are located so that the shield 22 may be folded into a rectangular package that can fit into a standard cabinet, for example on a 20"×24" shelf.

Each hinge 50, for example, may be constructed as shown in FIG. 9 by providing a slit 52 through the resilient sheet 30 that is then covered with a flexible and substantially or comparatively non-resilient tape 55 providing a living hinge along that hinge line. Once unfolded within the bore 14, the hinges 50 may be constructed to communicate compressive force 35 while staying in alignment thus preventing the hinges from folding. Alternatively or in addition, each hinge 50 be stiffened, for example, by circumferentially extending braces, in one example, being relatively resilient and stiff polymer tubes or rods 56 slit on one side along their length to provide an opening that can be fit over the one or both longitudinally opposed, circumferentially extending edge of the hinge 50 to provide stiffness of that hinge 50. Such stiffening may be used preferentially on hinges 50 near the apex of the bore 14 which will be subject to a radial inward force from gravity. The tubes 56 may initially positioned such that the resilient sheet 30 is displaced from the hinges 50 and simply slid into place as needed.

The hinges may also be created by partially scoring the plastic sheet to create a thinner region which folds more easily than the surrounding material. Other contemplated methods of producing the hinges include create a score line, with cutting, pressing, or heating being examples of manufacture processes.

Referring now to FIG. 10 in one embodiment, the hinges 50a-50c may have hinge lines that are progressively increasingly tipped or angled with respect to the longitudinal axis 16. In this case, the hinges 50a-50c provide a non-rectangular folding of the shield 22, for example, as depicted in FIG. 11, that is somewhat less space efficient than the embodiment of FIG. 8. Nevertheless, as shown in FIG. 12 these tipped hinges 50, when the shield is deployed in a cylindrical form against the inner side of the bore 14, are curved along their length with a slight arch as they pass helically around the bore 14 which gives them stiffness against folding without the need for stiffening ribs or the like.

The shield may be deployed as multiple units within a scanner bore. In one embodiment, for a scanner with a long bore, e.g. 40" or longer, it may be desirable to install one shield from the front and another shield from the back of the scanner, with partial overlap in the bore center.

The shield may have additional pieces of semi-rigid material, the same as or similar to the material used in other components of the shield, to provide full coverage of the scanner bore interior when the actuator member is moved. For example, sliding the actuator into the scanner may expose an opening between the panel 32 edges. The panels may be shaped to provide full coverage of the bore, or additional pieces or pieces of material may be attached for this purpose.

Referring again to FIG. 11, in each of these embodiments an impervious disposal bag 51, marked with a biohazard symbol, may be attached to the inside of the resilient sheet 30 to provide a container into which the used shield 22 may be placed for disposal after use. The shield 22 may be shipped sealed in a pouch 53 in sterile condition, for example, using any of various mechanisms including but not limited to radiation, steam, or ethylene oxide following, for example, the recommendations of the American National Standards Institute (ANSI) and the Association For The Advancement Of Medical Instrumentation (AAMI) including but not limited to: ANSI/AAMI ST79:2017; ANSI/AAMI/ISO 11135:2014; ANSI/AAMI/ISO 11137-2:2013; ANSI/AAMI/ISO 11137-3:2017 all hereby incorporated by reference.

Referring now to FIGS. 13 and 14, in one embodiment, the outer surface of the shield 22 may contact the interior surface of the bore 14 at a set of longitudinally parallel, radially extending ribs 54 spaced at equal circumferential angles about the axis 16 on the outer surface of the sheet 30. The ribs 54 provide bracing of the shield 22 against the bore 14 while also providing between the ribs 54 a space for the conduction of cooling air between the resilient sheet 30 and the inner wall of the bore 14 that may be required by some radiology scanners 10. In one embodiment, the ribs 54 may be formed from outwardly convex creases formed in the sheet 30, for example, by a thermoforming process during manufacture and may separate other portions of the sheet 30 from the inner wall of the bore 14 by a gap of approximately one to 1.5 inches. The resilient sheet 30 may also provide for one or more panels 58 covering openings in the resilient sheet 30, the panels presenting a filter material allowing for the passage of air but not pathogens, for example, using an N95 type filtration material. Such panels 58 may be aligned with fans or blower ports 60 or other radiology machine features such as microphones or cameras, opening from the walls of the bore 14.

Figure 15:
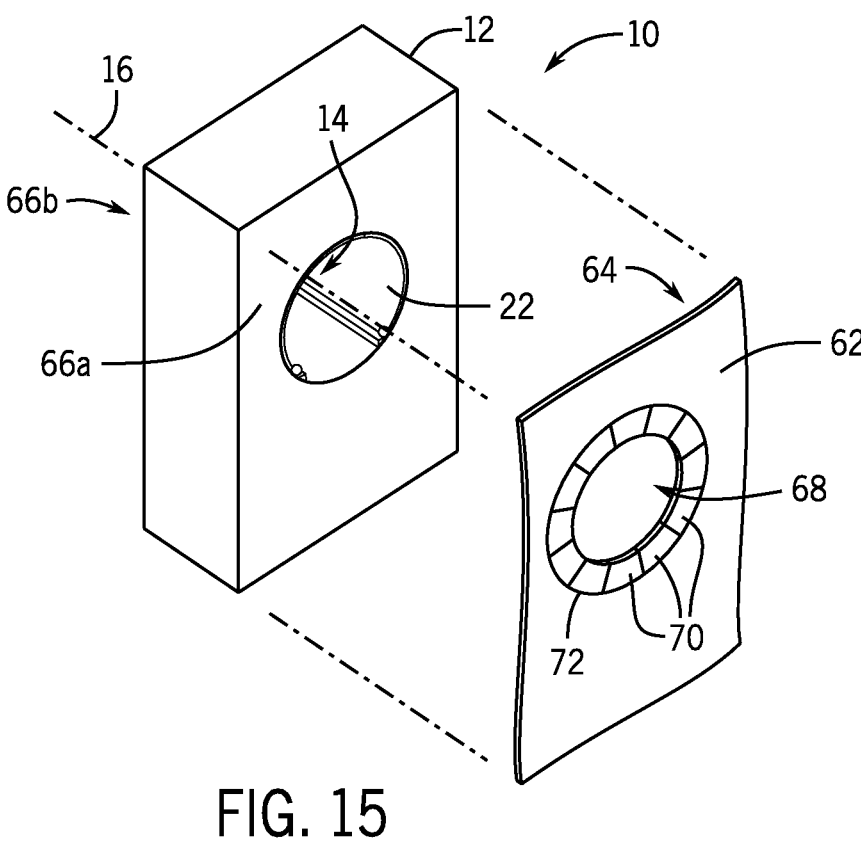
FIG. 15 is a simplified perspective view of a radiology scanner holding a shield of the present invention as used with supplemental shielding material to provide protection to the face of the radiology scanner.
Figure 16:
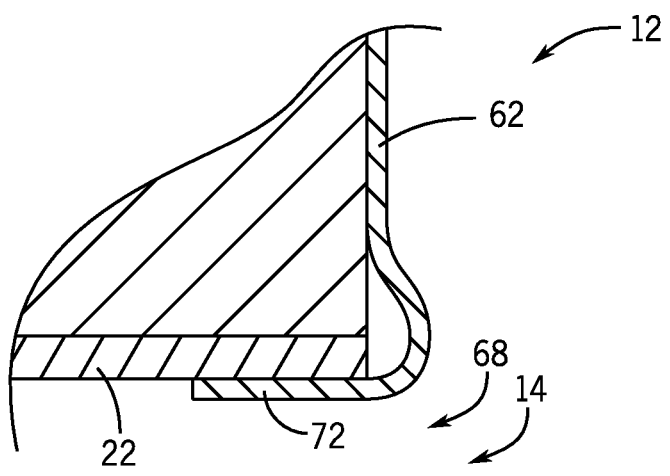
FIG. 16 is a fragmentary elevational cross-section in a plane of the longitudinal axis showing a folding of the supplemental shield material of FIG. 15 over the shield fitted within the bore of the radiology scanner.

Referring now to FIGS. 15 and 16, the shield 22 of the present invention may be used with a supplemental shield 62, for example, the latter being a flexible non-resilient polymer material, for example, similar in thickness and material to a standard surgical shield, having a removable or releasable adhesive material 64 on an inner surface to be adhered to a front wall 66a or rear wall 66b of the housing 12 of the radiology scanner 10 around the bore 14. In this respect, the supplemental shield 62 may substantially cover the walls 66 except for a central cut out 68 in the supplemental shield 62 ringed by a set of adhesive tabs 70 extending radially inward from a circular perimeter 72 equal to the diameter of the bore 14 and aligned therewith. The adhesive tabs 70 may be folded inward over the longitudinal ends of the inner surfaces of the shields 22 when the supplemental shield 62 is adhered to a wall 66 to provide a substantially continuous shielding surface over a wall 66 and bore 14 of the radiology scanner 10. The adhesive material may also be provided as strips or rectangular regions placed axially to provide partial or total coverage of the shield exterior facing the bore. For shipping, the adhesive of the supplemental shield 62 may be covered with a release liner that can be removed prior to installation.

Figure 17:
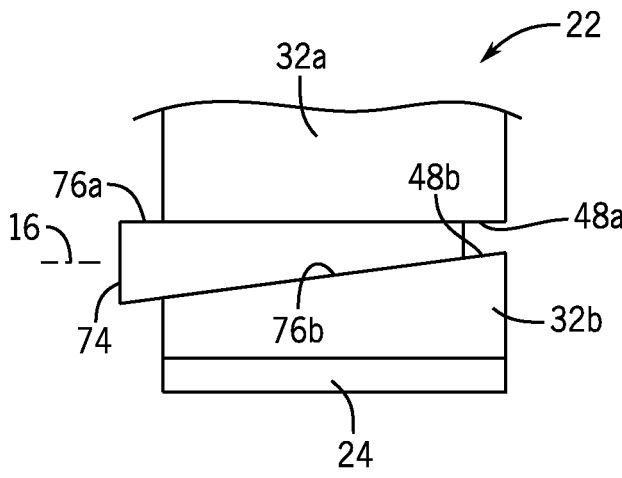
FIG. 17 is a fragmentary panoramic view similar to FIG. 2 showing an alternative adjustment structure for the shield employing a wedge for moving the shield from a first relaxed state to a second compressed state within the bore.
Figure 18:
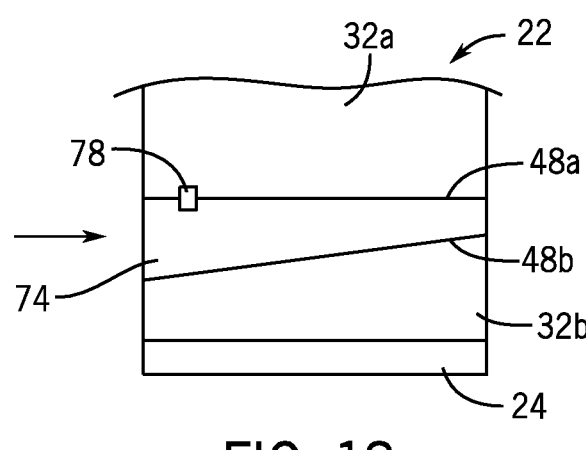
FIG. 18 is a figure similar to FIG. 17 showing the shield in the expanded state.
Figure 19:
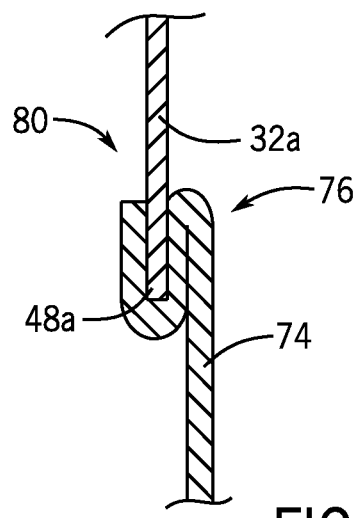
FIG. 19 is a fragmentary cross-sectional view perpendicular to the longitudinal axis of the wedge of FIGS. 17 and 18 showing a groove for a connecting it to the abutting shield material.

Referring now to FIGS. 17, 18 and 19, it will be appreciated that the toggle mechanism, for example, shown in FIGS. 2, 5, 7 and 8, may be implemented in alternative different ways while still providing adjustable circumferential expansion of the shield 22 to fit the bore 14. In one alternative embodiment, portions 32a and 32b of the resilient sheet 30 may be separated by a longitudinally extending wedge 74 in the shape of a triangle or trapezium having an edge 76b canted with respect to the longitudinal axis 16 and sliding along an edge 48b of portion 32b having the opposite angle of cant. An opposite edge 76a of the wedge 74 from canted edge 76 may be either parallel to the longitudinal axis 16 (to contact a similarly parallel edge 48a of portion 32a) or canted in the opposite direction to edge 76a (to contact a reverse canted edge 48a of portion 32a). Longitudinal movement of the wedge 74 will cause movement of the edges 48a and 48b in a similar manner as the toggle links 36 albeit without the changing mechanical advantage. When the wedge-shaped actuator panel is moved longitudinally, it will move the panel 32 edges either toward each other when the wedge shaped panel is moved so the narrow end of the wedge moves into the scanner bore, or apart from one another when the wide edge of the wedge moves into the bore. An adhesive strip may be used to lock the wedge 74 with respect to one or both of the portions 32.

Engagement between the wedge 74 and the portions 32 may be provided by equipping the upper and lower edges 76 of the wedge with guide slots 80 receiving the corresponding edges 48 therein for sliding engagement as shown in FIG. 19.

There may be a mechanical linkage to place and hold the wedge in proximity to the panel 32 edges, thus preventing the wedge from coming apart from the panel(s) 32 and creating a gap where the inner bore of the scanner is bare. Any mechanical linkages will permit the wedge to slide back and forth relative to the panels 32.

The mechanical linkages may consist of strips, slots, pins, rivets, or other bearing surfaces. The mechanical linkages shall conform to the same guidelines for non-conductivity and radiotranslucency as the rest of the device.

Generally, the resilient sheet 30 in all embodiments may have a thickness that resists buckling when in contact with a bore diameter of 30 inches and compressed with 0.5 pounds of circumferential force, in some embodiments, the shield 22 in a relaxed state will be substantially in a flat longitudinal dimension of at least 30 inches and in a transverse dimension of at least 45 inches (at least 50% of the circumference of a 30 inch diameter bore). In all embodiments, the dimensions, material, and construction techniques shall be sufficient to provide mechanical support of the shield within and against the scanner bore.

The installation of additional supporting devices on or within the scanner may add support to the device or aid in its alignment.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A shield for a medical scanner having a cylindrical bore extending along an axis, the shield comprising:

a resilient sheet sized to fit loosely within the bore of a medical scanner in a first relaxed state and then to flex outward against an inner circumference of the bore in a second compressed state upon circumferentially directed compressive forces on the resilient sheet, the resilient sheet in the second compressed state extending along an axial length of the bore and over at least 50% of the inner circumference of the bore, the resilient sheet in the first relaxed state presenting circumferentially opposed and circumferentially spaced apart axially extending edges extending within the bore over the axial length of the bore bounded by circumferentially extending edges; and a compressor adapted to slide axially with respect to the resilient sheet and along at least one axially extending edge to urge the at least one axially extending edge in a circumferential direction following the extent of the resilient sheet and causing the resilient sheet to move outward against the inner circumference of the bore;

wherein the shield has a first and second portion defining first and second circumferentially spaced edges, wherein the compressor is a connector adjustably joining the first and second circumferentially spaced edges to change a separation between the first and second circumferentially spaced edges to provide a circumferential compression of the resilient sheet in the second compressed state, wherein the connector provides a single actuator member extending along the bore and movable axially along the bore between a first and second position so that the axial movement causes the first and second circumferentially spaced edges to move between a first separation with the resilient sheet fitting within the inner circumference of the bore without pressing against the inner circumference of the bore, to a second separation with the resilient sheet pressed against the inner circumference of the bore in the second compressed state.

2. The shield of claim 1 wherein the resilient sheet is self-supporting on opposed edges against inner walls of a 20 inch diameter cylindrical bore.

3. The shield of claim 1 wherein the resilient sheet includes an inner coating of hydrophilic polymer.

4. The shield of claim 1 wherein the resilient sheet includes an inner antimicrobial coating.

5. The shield of claim 1 wherein at least a portion of the resilient sheet includes an outer coating of a releasable adhesive.

6. The shield of claim 1 wherein the single actuator member is a wedge extending parallel to an axis of the bore along an inner wall of the bore so that axial movement of the wedge wedges the first and second circumferentially spaced edges apart.

7. The shield of claim 1 wherein the single actuator member provides multiple points of contact along the axial length of the single actuator member to the first and second circumferentially spaced edges to provide circumferentially expanding force along the resilient sheet.

8. The shield of claim 1 further including a lock holding the single actuator member with respect to the first and second circumferentially spaced edges in the second position.

9. The shield of claim 8 wherein the lock is selected from the group consisting of a hook and loop fastener and a pressure sensitive adhesive joining the single actuator member and at least one of the first and second circumferentially spaced edges of the resilient sheet.

10. The shield of claim 1 wherein axial movement of the single actuator member between the first position and second position provides a change in the separation of the first and second circumferentially spaced edges of at least one cm.

11. The shield of claim 1 wherein the single actuator member communicates with the first and second circumferentially spaced edges through a set of toggle links.

12. The shield of claim 1 wherein the resilient sheet includes at least one panel of an air permeable filter material.

13. The shield of claim 1 wherein an outer surface of the resilient sheet includes a plurality of ribs to provide an air gap between the resilient sheet and the bore in the second compressed state.

14. The shield of claim 1 wherein the resilient sheet includes hinges extending along an axis of the bore allowing for non-resilient folding of the resilient sheet.

15. The shield of claim 14 wherein the hinges follow helical lines with respect to the cylindrical bore in the second compressed state.

16. The shield of claim 1 wherein the resilient sheet is transparent.

17. The shield of claim 1 wherein the shield is free from electrically conductive material.

18. The shield of claim 1 wherein the resilient sheet is adapted to provide a total linear attenuation of x-rays from the medical scanner along a line of radius of the bore in the second compressed state of less than or equal to that of a thickness of 0.8 cm of distilled water.

* * * * *